United States Patent [19]

Koch et al.

[11] Patent Number: 4,465,067
[45] Date of Patent: Aug. 14, 1984

[54] OXYGEN INSUFFLATION DEVICE

[75] Inventors: Jochim Koch, Hollenbek; Wolfgang Drews, Reinfeld, both of Fed. Rep. of Germany

[73] Assignee: Drägerwerk Aktiengesellschaft, Fed. Rep. of Germany

[21] Appl. No.: 418,981

[22] Filed: Sep. 16, 1982

[30] Foreign Application Priority Data

Apr. 24, 1982 [DE] Fed. Rep. of Germany ....... 3215466

[51] Int. Cl.$^3$ ............................................. A61M 15/08
[52] U.S. Cl. ........................ 128/207.18; 128/DIG. 26
[58] Field of Search ...................... 128/207.18, 204.18, 128/DIG. 26; 351/117, 122

[56] References Cited

U.S. PATENT DOCUMENTS 2,135,800 11/1938 Davignon .......................... 351/122
2,735,432 2/1956 Hudson ........................ 128/DIG. 26
4,363,323 12/1982 Geiss ............................. 128/207.18

FOREIGN PATENT DOCUMENTS 1124404 10/1956 France ............................. 128/207.18

Primary Examiner—Henry J. Recla
Attorney, Agent, or Firm—McGlew and Tuttle

[57] ABSTRACT

An oxygen insufflation device for wearing on the head of a person comprises a head engaging frame similar to a spectacle frame including a front portion and a side temple portion engaged on each side of said frame terminating in respective ear engaging ends. The front member is engaged with the front portion of the frame and has a nose feed engageable over the person's nose and a downwardly extending portion terminating in a nose plug which is engageable into a single nostril. A flexible connection for supplying oxygen is connected into the frame at one of the temple portions and an oxygen flow passage is defined from this flexible connection through the associated temple portion and along the front of the frame and down said front member in the downwardly extending portion and terminates in a discharge opening in the nose plug. The frame advantageously includes a flexible connection between the front portion of the frame and the temples in the form of flexible links which are made from corrugated tube stock. Ear engaging portions comprise bows which are made of helically wound flat wires enclising a spring construction within the wires. The front portion of the device advantageously includes a flexible angular tubular member terminating in the nose seat.

8 Claims, 3 Drawing Figures

OXYGEN INSUFFLATION DEVICE

FIELD AND BACKGROUND OF THE INVENTION

This invention relates in general to oxygen supply devices for respiratory systems and in particular to a new and useful device for wearing on the head of a person providing means for supplying oxygen into the nose of the wearer.

In oxygen therapy, a mixture of oxygen and air is supplied to the patient. Nasal insufflation has proved a method very agreeable to the patient. In this method, the oxygen is supplied through a nose catheter, a cannula, or through insufflation spectacles.

A prior art nose cannula for dispersing oxygen to a patient comprises a body of a flexible material having a flattened top surface wherefrom two hollow, tubular extensions spaced apart project upwardly. The cavities of the extensions communicate with a gas conduit extending lengthwise through the flattened body. At both sides, a flexible tube is connected to the gas conduits. Both flexible tubes are connected to a common oxygen source. In use, the tubular extensions are introduced into the nostrils, with the flat top surface of the body applying from below against the nostrils and spanning them. The flexible tubes are trained at both sides of the patient's head around the ears and are detachably united below the chin, to obtain a satisfactory fixation. For long-term use, it is troublesome that because of the plugging of both nostrils, exhalation is possible only through the mouth. At the same time, the tubular extensions inserted in the nostrils are annoying. The tubes, chiefly extending over the moving portions of the patient's face, are disturbing for the speech and have a disfiguring effect (German Pat. No. 20 55506).

Another prior art design are oxygen insufflation spectacles comprising a frame as for glasses, which extends over the roof of the nose, the nose sides, and below the eyes, to be secured by bows behind the ears. The frame is made of tubular material and provided at one side with a nipple for oxygen supply. Below each of the eyes, a nose tube is connected which is curved and reaches up to the nostril and carries a short rubber tube to be inserted into the nostril. For long-term use, the oxygen spectacles produce a disfiguring impression and interfere with wearing eyeglasses. The flexible tubes inserted in the nostrils are uncomfortable. The nose is not closed and therefore, because of the exhalation, only a moderate enrichment with oxygen can be obtained. (Dragerwerk prospectus 618, August 1964).

SUMMARY OF THE INVENTION

The invention is directed to oxygen insufflation spectacles in which the above-mentioned disadvantages are eliminated and which facilitate the patient's breathing by supplying the respiratory ducts with a mixture enriched in oxygen and may well be conformed to the shape of the patient's head, and do not hinder wearing of eyeglasses.

In accordance with the invention an oxygen insufflation device for wearing on the head of a person comprises a head engaging frame which includes a front portion and a side temple portion engaged on each side of the frame and which terminates in respective ear engaging ends or bows. The front member is engaged with the front part of the frame and has a nose seat engageable over the person's nose and a downwardly extending portion which terminates in a nose plug which engages into a single nostril. Members of the frame and the front member are advantageously mated, in order to define an oxygen flow passage which is connected to an exterior flexible oxygen supply line which has means for controlling the oxygen flow and includes a clip for securing it to the wearer's garment. A flow passage extends from the flow connection through a temple part and a portion of the front member of the frame downwardly through an angular tubular member at the front of the frame and terminates in a nose plug which discharges into a wearer's nostril.

The advantages of the invention are that the spectacles are very well adaptable to any face, whereby they offer a very comfortable wear, and, primarily, that the oxygen is blown in only through one nostril which, otherwise, is completely closed. The patient can use the other nostril for unobstructed exhaling, while at the same time further oxygen is blown into a part of the respiratory ducts and is instantly available for, and ensures, a high oxygen concentration. The suitable shape of the frame follows the natural horizontal and vertical division of the human face and extends from the front to the root of the nose. The flexible oxygen supply tube can be run inconspicuously behind the ear. The disfiguration of the aspect of the face is avoided. The location of the front portion at a high level and the spacing of the nose connection from the root of the nose make possible a simultaneous wear of eyeglasses.

To be able to control the oxygen supply, a development of the invention provides that a flow control device is connected in the flexible oxygen supply tube and equipped with a clip, to simply be secured to the wearer's garment. Thereby, any tension forces which might be produced, for example, by the flexible tube being caught somewhere, are taken up at the same time and are not transmitted to sensitive body parts, such as to the nose or ear.

Further developments of the invention relate to a suitable selection of material.

The advantages resulting from the invention make it possible to supply a patient with breathing oxygen without hindering, or disfiguring the aspect of, the patient's face.

Accordingly it is an object of the invention to provide an improved device for supplying oxygen to a person which includes a spectacle-like frame which is engageable on the head of the wearer and includes an internal passage extending through a nose seat and downwardly to a hollow nose plug which engages in that person's nose and which is simple in design, rugged in construction and economical to manufacture.

For an understanding of the principles of the invention, reference is made to the following description of a typical embodiment thereof as illustrated in the accompanying drawings.

DESCRIPTION OF THE PREFERRED EMBODIMENT

Figure 1:
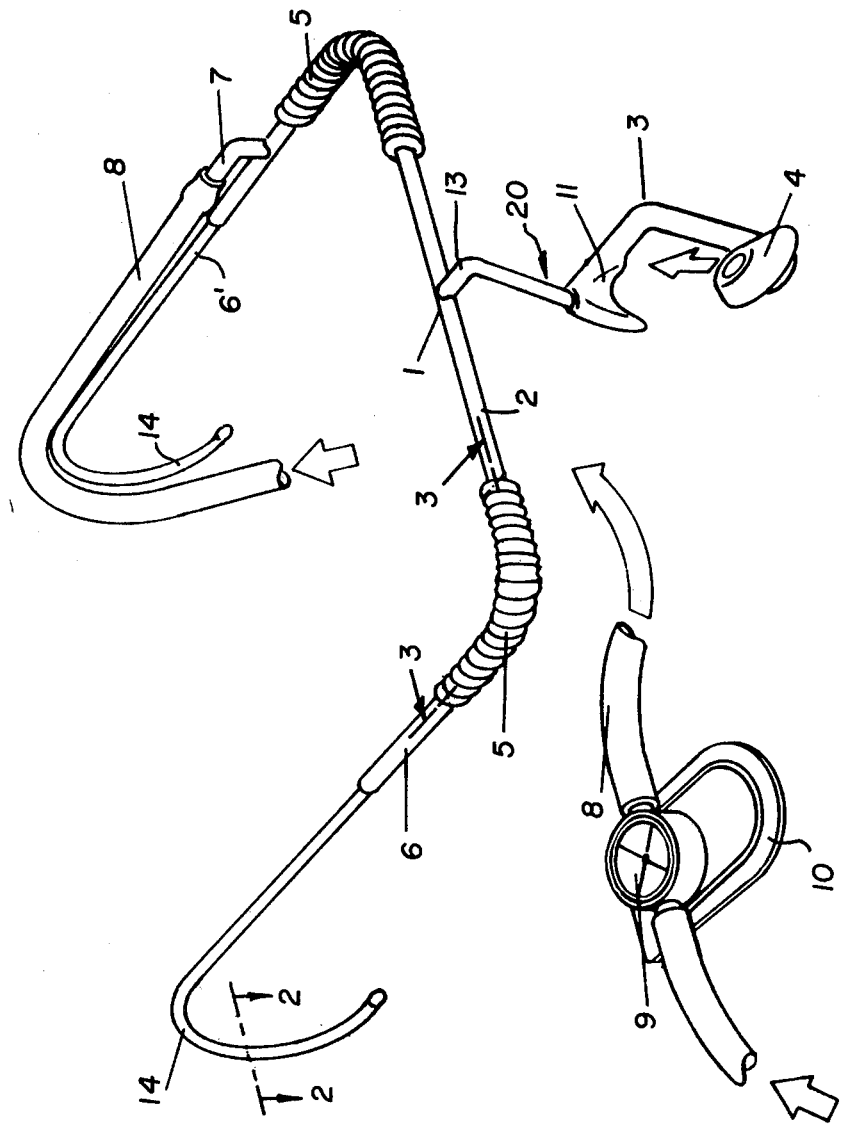
FIG. 1 is a front top perspective view of an oxygen supply device constructed in accordance with the invention.

Referring to the drawings in particular the invention embodied therein comprises an oxygen insufflation device generally designated 20 which comprises a head engaging frame which includes a front portion 2 and side temple portions 6, 6' engaged on each side of the frame and which terminate in respective ear engaging ends or bows 14, 14'.

The insufflation spectacles 1 are designed as a frame comprising the front portion 2, a flexible nose connection 3 terminating in a hollow nose plug 4, and temples 6, 6' which are connected through flexible links 5, 5 to the front portion. One of temples 6' is provided with a connection 7 formed to project above the temple in a direction parallel thereto and intended for connecting a flexible oxygen supply tube 8. Connection 7 is connected to a tube part of temple portion 6'. A flow control device 9 which can be secured by a clip 10 to a wearer's garment makes it possible to monitor the oxygen supply.

The flexible nose connection 3 is an injection-molded part of a plastic known per se. This connection is formed with a top nose engagement part or nose seat 11 which is followed by or includes a hollow conduit unilaterally connected thereto and terminating in a nose plug 4 which fits into one nostril of the wearer. From the nose seat 11, connection 3 communicates with the front portion 2 through an angled and saliently extending tubular member 13 which is made of a flexible material. The flexible links 5 are made of corrugated tube lengths.

Figure 2:
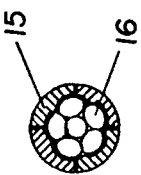
FIG. 2 is a sectional view taken along the line 2—2 of FIG. 1.
Figure 3:
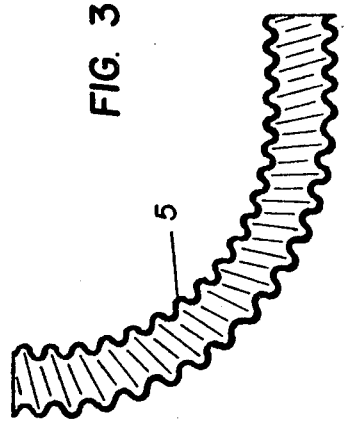
FIG. 3 is a sectional view taken along the line 3—3 of FIG. 1.

Temples, 6' terminate in a bow portion or ear engaging parts 14 of helically wound flat wires 15 as shown in FIG. 2. The wires are bent into a spiral by an enclosed spring 16 comprising a plurality of spring wires.

Due to the flexible links 5, the bow portion 14, and the flexible nose connection 13, insufflation spectacles resiliently conform to the shape of the user's head. The determining parameters are the width of the head, the distance between the nose and the ear, and the length of the nose. Front portion 2 provided at a high level extends above the extension of usual eyeglass mounts (that is, above the eyes), and sufficient space is left inside of angled tubular member 13 for eyeglass bridges, so that insufflation spectacles 1 make it possible to wear eyeglasses in addition.

While a specific embodiment of the invention has been shown and described in detail to illustrate the application of the principles of the invention, it will be understood that the invention may be embodied otherwise without departing from such principles.

What is claimed is:

1. An oxygen insufflation device for wearing on the head of a person comprising a head engaging frame including a tubular front portion (2), a first tubular flexible link (5) connected to one side of said front portion, a second tubular flexible link connected to an opposite side of said front portion, a first tubular temple portion (6) having a first ear-engaging part (14) at one end thereof and connected to said first flexible link at an opposite end of said first tubular temple portion, a second tubular temple portion (6) having a second ear-engaging part (14) at one end thereof and connected to said second flexible link at an opposite end of said second temple portion, a tubular member (13) connected to said tubular front portion at a location intermediate of said one and said opposite side of said tubular front portion, said tubular member having a selected length and connected to said tubular front portion at one end thereof, a nose seat (11) connected to said tubular member at an opposite end thereof, said nose seat shaped to have opposite sides adapted for engaging the bridge of a person's nose, a flexible tubular nose connection (3) connected to one of said opposite sides of said nose seat, a hollow nose plug connected to said flexible tubular nose connection at an end of said flexible tubular nose connection remote from said nose seat, said flexible tubular nose connection having a length so that with the nose seat engaged on the bridge of a person, the nose plug is engaged in one nostril of the person, and a gas connection (7) connected to said first tubular temple portion for supplying breathing gas to said first tubular temple portion, through said first tubular flexible link, said tubular front portion, said tubular member and said flexible tubular nose connection to said hollow nose plug, said selected length of said tubular member being chosen to maintain said front portion above the eyes of a person when said nose seat is engaging the bridge of the person's nose.

2. A device according to claim 1, wherein said tubular member has an angle therein between said front portion and said nose seat for positioning said nose seat forwardly of said front portion with respect to said first and second temple portions which are positioned rearwardly of said front portion.

3. A device according to claim 2, wherein said gas connection is connected to said first temple portion to extend upwardly of said first temple portion with respect to said tubular member which extends downwardly of said first temple portion and said front portion, and a flexible supply tube connected to said gas connection and extending over at least said first ear-engaging part of said temple portion.

4. A device according to claim 3, wherein each of said first and second ear-engaging parts comprise a spirally-bent spring.

5. A device according to claim 3, including a flow control device connected to said flexible supply tube at a position thereon spaced from said gas connection and clip means connected to said flow control device for clipping said flow control device and said flexible supply tube at a person's garment.

6. A device according to claim 3, wherein each of said first and second temple portions have a tube part connected to each of said first and second flexible links respectively, said gas connection connected to said tube part of said first temple portion, each of said first and second flexible links comprising a corrugated tube forming a hollow passage.

7. A device according to claim 6, wherein said front portion comprises a tube adapted to extend at least partly across the face of a person wearing the device.

8. A device according to claim 7, wherein said hollow nose plug is molded to fully plug one nostril of a person's nose when said nose seat is engaged on the bridge of a person's nose.

* * * * *